US006767349B2

(12) United States Patent
Ouchi

(10) Patent No.: US 6,767,349 B2
(45) Date of Patent: Jul. 27, 2004

(54) BIPOLAR FORCEPS FOR ENDOSCOPES

(75) Inventor: Teruo Ouchi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/084,337

(22) Filed: Feb. 28, 2002

(65) Prior Publication Data

US 2002/0123667 A1 Sep. 5, 2002

(30) Foreign Application Priority Data

Mar. 1, 2001 (JP) ........................................ 2001-056752

(51) Int. Cl.$^7$ ............................................ A61B 18/14
(52) U.S. Cl. ............................ 606/51; 606/49; 606/50; 606/52; 606/205; 606/208
(58) Field of Search .......................... 606/49–52, 205, 606/208

(56) References Cited

U.S. PATENT DOCUMENTS

| | | | | |
|---|---|---|---|---|
| 5,762,613 A | * | 6/1998 | Sutton et al. ............... | 600/564 |
| 5,853,412 A | * | 12/1998 | Mayenberger ............... | 606/51 |
| 6,013,095 A | | 1/2000 | Ouchi | |
| 6,033,424 A | | 3/2000 | Ouchi | |
| 6,063,086 A | * | 5/2000 | Benecke et al. ............. | 606/51 |
| 6,193,737 B1 | | 2/2001 | Ouchi | |
| 6,283,924 B1 | | 9/2001 | Ouchi | |

FOREIGN PATENT DOCUMENTS

| | | |
|---|---|---|
| JP | 4-55081 | 2/1992 |
| JP | 11-19087 | 1/1999 |
| JP | 11155874 | 6/1999 |
| JP | 11155875 | 6/1999 |
| JP | 11155876 | 6/1999 |
| JP | 11155877 | 6/1999 |
| JP | 11155878 | 6/1999 |
| JP | 2000271128 | 10/2000 |

OTHER PUBLICATIONS

English Language Translation for 2000–271128.
English Language Abstract for 11–155878.
English Language Abstract for 11–155877.
English Language Abstract for 11–155876.
English Language Abstract for 11–155875.
English Language Abstract for 11–155874.
Engish Language Abstract 11–19087.
English Language Translation for 4–55081.

* cited by examiner

Primary Examiner—Roy D. Gibson
Assistant Examiner—Aaron Roane
(74) Attorney, Agent, or Firm—Greenblum & Bernstein, P.L.C.

(57) ABSTRACT

There is provided a bipolar forceps for endoscopes that includes a clevis, two shafts, and two end effectors. The clevis has two arms that form a slot between them. The shafts are sustained between the two arms spaced apart from each other. Each of the end effectors is pivotably attached to a different one of the two shafts, respectively, such that the end effectors are able to move in a scissor-like action. The end effectors being made of conductive material. Thus the end effectors can be utilized as electrodes for applying a high frequency voltage between them.

13 Claims, 5 Drawing Sheets

BIPOLAR FORCEPS FOR ENDOSCOPES

BACKGROUND OF THE INVENTION

The present invention relates to a bipolar forceps for endoscopes, and more particularly, to a bipolar forceps having two end effectors between which high frequency voltage is to be applied.

Endoscopic operation such as cutting and/or coagulating internal tissues are frequently performed using a mono-polar forceps. When the mono-polar forceps is employed, one internal electrode is inserted into a patient through an endoscope, while another ground electrode is placed on the skin of the patient. A high frequency voltage is applied to the internal electrode so that the tissue at the internal electrode is cut and/or coagulated by electric current flowing between the internal electrode and the ground electrode.

The electric current, however, does not flow only between the internal electrode and the ground electrode but also to any other conductors that are in contact with the patient, if there is any, and this kind of current flow decreases the amount of electric current that affects the operation of the tissue. Further, electric current may also flow through a surgeon who unintentionally touches the patient during the operation.

Japanese Patent application provisional publication P2000-271128 discloses a bipolar forceps for endoscopes that overcomes the above mentioned problems of the mono-polar forceps. The disclosed bipolar forceps includes a pair of electrodes provided at the distal end of a flexible sheath, which is remotely operated from the proximal end of the flexible sheath to open and close in a scissors-like action. High frequency voltage is applied between the two electrodes to cut and/or coagulate the internal tissue located between the electrodes.

It is important for the bipolar forceps to ensure electric insulation between the two electrodes, which is difficult since the electrodes are located in the immediate vicinity of each other. In order to achieve the electric insulation between the electrodes, the forceps disclosed in the above mentioned Japanese application employs electrodes made of nonconductive materials such as plastics and ceramics, partially applied with metal coatings on the surface thereof by means of vaporization.

Electrodes made of plastics or ceramics, however, are easy to be damaged during repetitive use due to their insufficient strength. In addition, the metal coatings on the electrodes tends to wear out due to friction between the electrodes and endoscope during the advance and retraction of the forceps through the endoscope.

SUMMARY OF THE INVENTION

The present invention provides the advantage in that, in a bipolar forceps for endoscopes, electric insulation between the electrodes is structurally achieved and thus electrodes made of materials having practically sufficient strength for repetitive use can by employed.

According to embodiments of the invention, there is provided a clevis, two shafts, and two end effectors. The clevis has two arms that form a slot between them. The shafts are sustained between the two arms spaced apart from each other. Each of the end effectors is pivotably attached to a different one of the two shafts, respectively, such that the end effectors are able to move in a scissor-like action. The end effectors are made of conductive material. Thus the end effectors can be utilized as electrodes for applying a high frequency voltage between them.

Since the two end effectors are separately sustained by different shafts, respectively, short circuit does not occur between the end effectors during the application of high frequency voltage to them although the end effectors are made of conductive material.

The two shafts may be arranged in parallel to each other. Further, each of the shafts may be arranged to cross the slot perpendicularly.

Optionally, the two shafts may be located on opposite sides with respect to the center axis of said clevis, respectively. In this case, the two shafts may further be located at a same distance from the center axis of the clevis.

The shafts and/or the end effectors may be made of metal in order to increase the durability of the forceps. The clevis may be made of non-conductive material so that no short circuit between the end effectors will be established via the clevis.

Optionally, the bipolar forceps of the invention may include two cylindrical insulators each provided on a different one of the two shafts, respectively, in order to insulate the end effectors from the shafts. Such insulators prevent the short circuit between the two end effectors even when fluid adheres to and bridges the two shafts.

In the above case, the cylindrical insulator may cover the shaft over the entire width of the slot that is formed between the arms of the clevis in order to prevent the short circuit effectively.

Optionally, the cylindrical insulator may include a small outer diameter portion for fitting the end effector thereon. This small outer diameter portion may have an outer diameter smaller than the outer diameter of an adjacent portion of the cylindrical insulator for keeping the end effector in place.

In the above case, one of said two cylindrical insulators may have the small outer diameter portion at the end thereof located besides one of the two arms, and the other of said two cylindrical insulators may have the small outer diameter portions at the end thereof located besides the other of the two arms, so that the end effectors held by the shafts are located spaced apart also in the slot width direction.

Optionally, each of the end effectors may be bent between a distal end of the end effector and a portion being attached to the shaft such that at least the distal ends of the end effectors meet each other when the end effectors are closed.

BRIEF DESCRIPTION OF THE ACCOMPANYING DRAWINGS

DETAILED DESCRIPTION OF THE EMBODIMENTS

Hereinafter, a bipolar forceps 100 for endoscopes according to an embodiment of the invention will be described with reference to the accompanying drawings.

Figure 1:
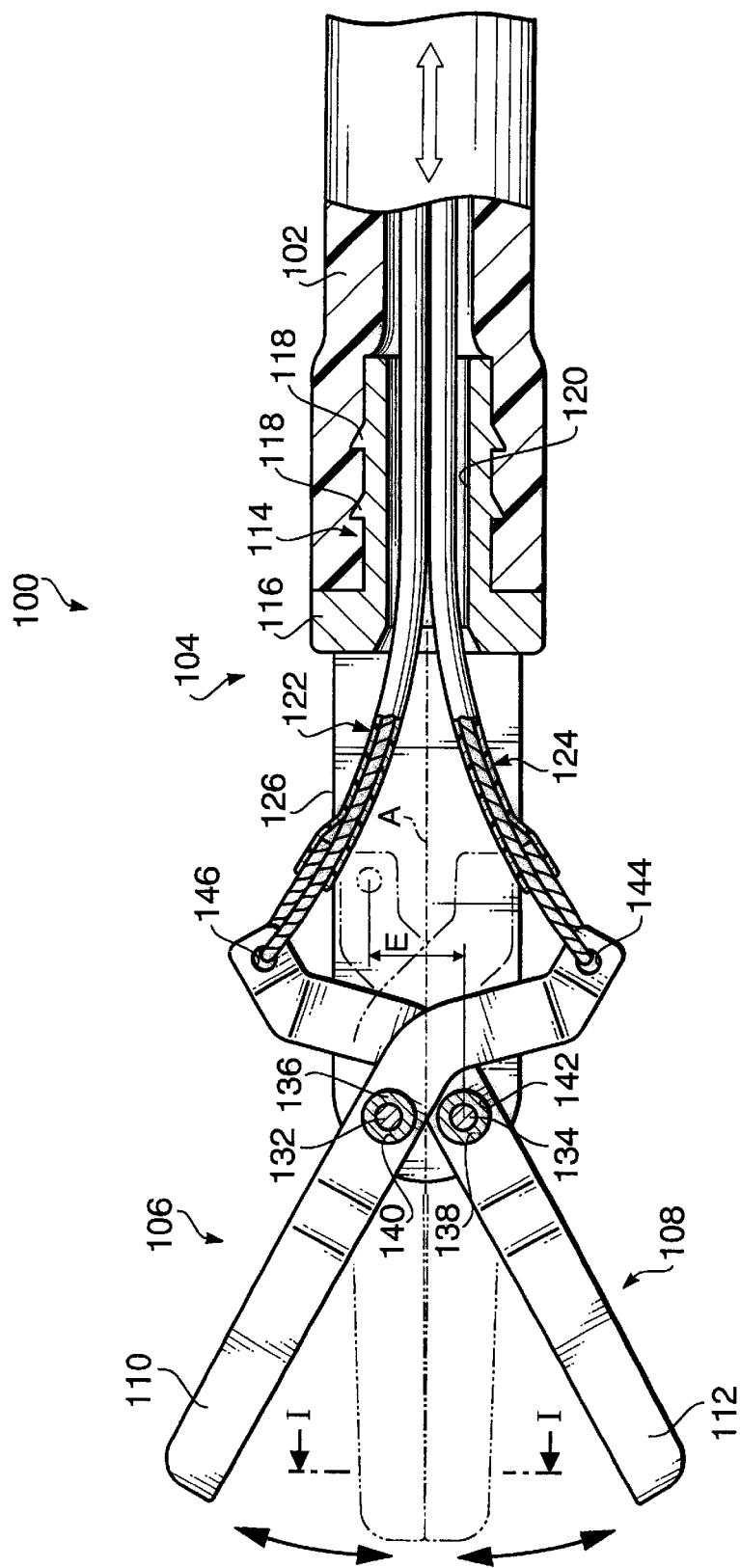
FIG. 1 is a partially cross-sectional side view of a distal end portion of a bipolar forceps for endoscopes according to an embodiment of the invention.
Figure 2:
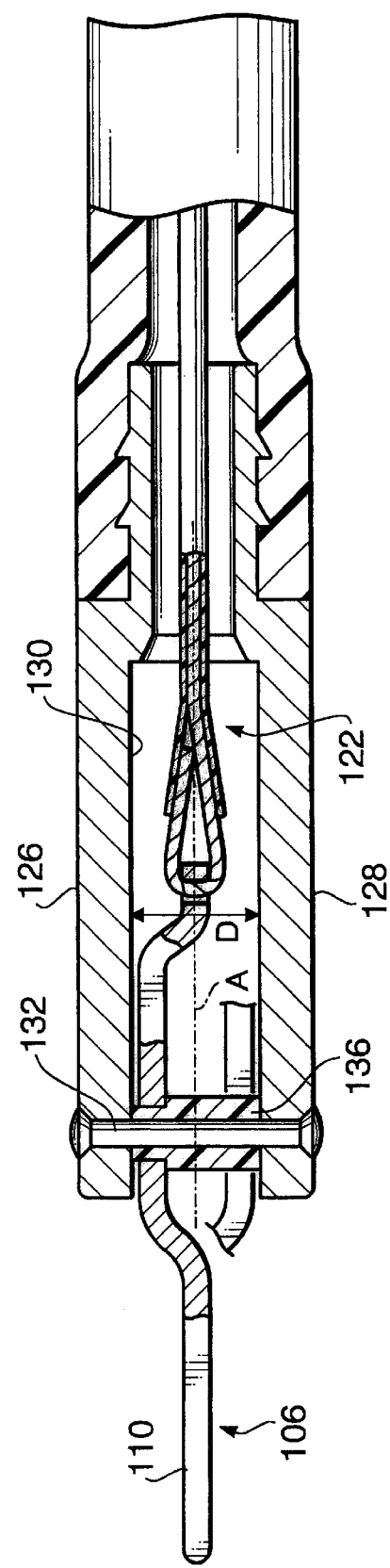
FIG. 2 is a partially cross-sectional top view of the distal end portion of the bipolar forceps of FIG. 1.

FIGS. 1 and 2 show a partially cross-sectional side view and a partially cross-sectional top view, respectively, of the distal end portion of the bipolar forceps 100 according to an embodiment of the invention. Note that FIG. 2 shows several different cross-sections together that are taken along different planes.

The bipolar forceps 100 includes a flexible sheath 102, a clevis 104, and a pair of end effectors 106 and 108 with opposing end portions, or jaws 110 and 112.

The flexible sheath 102, which is to be inserted through a lumen of an endoscope, has a diameter of 2 mm, 1–2 m long, for example, and is made of an electrical insulating material such as tetrafluoroethylene resin tube.

The clevis 104, made of electrical insulating material such as rigid plastic, is attached to the distal end of the flexible sheath 102 by inserting its proximal end, or base portion 114, into the lumen of the flexible sheath 102. The base portion 114 of the clevis 104 is formed in a cylindrical shape with a flange 116 for limiting the length of the clevis 104 to be inserted into the flexible sheath 102.

A plurality of spikes 118 are formed on the outer peripheral surface of the base portion 114 that engage with the inner surface of the flexible sheath 102 and prevent the base portion 114 to be pulled out therefrom. A lumen 120 is formed through the base portion 114 along a center axis A of the clevis 104 that allows a pair of conductive wires 122 and 124 to pass therethrough.

Two arms 126, 128 are extending forwards from the base portion 114 of the clevis 104 to form a slot 130 of a constant width D between them.

Two shafts 132, 134 are fixed to the arms 126, 128 in the vicinity of the distal end of the arms 126, 128 such that the shafts 132, 134 perpendicularly cross the slot 130. The two shafts 132, 134 are located in opposite side with respect to the center axis A of the clevis 104, respectively, in parallel to each other and at same distance from the center axis A. In the present embodiment, the shafts 132, 134 are made of a material having high rigidity such as stainless steel or other metals.

The shafts 132, 134 are covered over the entire with of the slot 130 with cylindrical insulators 136, 138 made of electrically insulating material. The cylindrical insulators 136, 138 loosely fit around the shafts 132, 134 so that the cylindrical insulators 136, 138 can rotate around respective shafts 132, 134. One of the ends of each cylindrical insulator (136, 138) is formed to have an outer diameter smaller than the rest portion of the cylindrical insulator (136, 138). The cylindrical insulators 136, 138 are arranged on the shafts 132, 134 such that the small diameter end of one of the cylindrical insulators is located besides one of the two arms 126, 128 and that of the other cylindrical insulator is located besides the other arm.

The end effectors 106, 108 are made of a conductive material such as stainless steel so that the end effectors 106, 108, in particular the jaws 110 and 112, can be used as electrodes. Each of the end effectors 106, 108 includes a proximal portion, a distal portion, or jaw, and a middle portion located between the proximal and distal portions. A pivot hole (140, 142) is formed in the middle portion, which can fit on the small diameter end of the cylindrical insulator (136, 138). The end effectors 106, 108 are pivotably attached to the distal end of the clevis 104 by fitting the pivot hole (140, 142) of each end effectors on the small diameter ends of different cylindrical insulators (136, 138). Thus, the two end effectors 106, 108 are separately sustained by each shafts 132, 134.

As best seen in FIG. 2, the end effectors 106, 108 are bent at both side of the middle portion such that the middle portion can be located at the side of slot 130 while both proximal and distal portions are located on a plane that passes through the center of the slot 130. When the end effectors 106, 108 are pivoted around the respective shafts 132, 134, the distal ends of the end effectors 106, 108, or jaws 110 and 112, move in a scissor-like action and thereby open and close as shown in FIG. 1 with solid lines and broken lines, respectively.

Figure 3A:
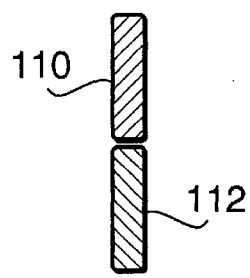
FIGS. 3A through 3D show examples of cross-sections of jaws of the bipolar forceps of FIG. 1 taken along line I—I.
Figure 3B:
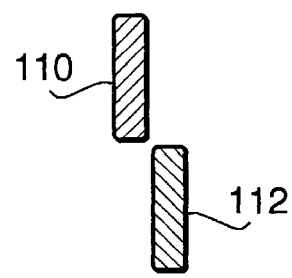
Figure 3C:
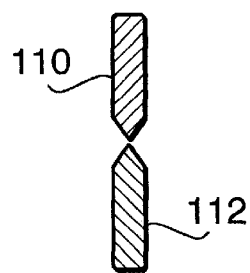
Figure 3D:
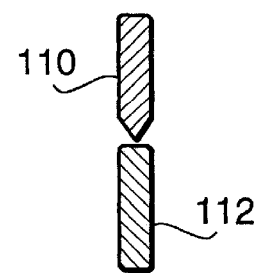

FIGS. 3A through 3D show examples of cross-sections of the jaws 110 and 112 in the closed position, taken along line I—I in FIG. 1. As shown in FIG. 3A, the jaws 110 and 112 may have rectangular cross-sections and be aligned so as to meet to each other when the jaws 110 and 112 are closed. In another example, as shown in FIG. 3B, the location of one of the jaws may be shifted laterally, in the slot width direction, with respect to the other jaw so that the two jaws 110 and 112 do not face each other when the jaws 110 and 112 are closed. In still another examples, one or both of the jaws 110 and 112 may have a sharp rim at the side that meets to the other jaw as shown in FIGS. 3C and 3D.

Now referring back to FIGS. 1 and 2, engaging holes 144, 146 are formed to the proximal end of the end effectors 106, 108 that engage with the distal ends of the wires 122, 124.

The wires 122, 124 are coated with electrically insulating material over its entire length except the distal ends. Each of the distal ends of the wires 122, 124 are passed through the engaging hole (144, 146) of different end effectors (106, 108), respectively, and then bent tightly in order to sandwich and make contact with the proximal end of the corresponding jaw.

The wires 122, 124 are passed through the lumen of the flexible sheath 102 and connected to a power supply (not shown) for applying high frequency voltage between the end effectors 106, 108 via the wires 122, 124.

The proximal ends of the wires 122, 124 are also connected to an operating unit (not shown) provided at the proximal end of the flexible sheath 102. The operating unit is operated to advance and retract the wires 122, 124 along the lumen of the flexible sheath 102. If the wires 122, 124 are advanced, then the end effectors 106, 108 pivot to open the jaws 110, 112, and if the wires 122, 124 are retracted, the end effectors 106, 108 pivot to close the jaws 110, 112. In some embodiments, the wires 122, 124 are bound together within the flexible sheath 102 such that the wires 122, 124 move integrally along the lumen of the flexible sheath 102 and thereby the jaws 110, 112 open and close symmetrically.

As best seen in FIG. 1, the proximal portion of each end effectors 106, 108 is bent such that the engaging hole (144, 146) and the pivot hole (140, 142) are located on opposite sides with respect to the center axis A of the clevis 104 regardless the jaws 110 and 112 are opened or closed. Due to this configuration, the distance E between the engaging hole (144, 146) and the pivot hole (140, 142) in the direction lateral to the arm (126, 128) is relatively large, and therefore the wires 126, 128 can apply relatively large rotating moment to the end effectors 106, 108.

The bipolar forceps 100 described above is inserted to a human cavity through an endoscope. The jaws 110, 112 are opened by retracting the wires 122, 124, and then guided by the endoscope to a target site of tissue or mucous membrane to be cut and/or coagulate. Then, the jaws 110, 112 are closed by advancing the wires 122, 124 so that the jaws 110, 112 sandwich the target site.

Figure 4A:
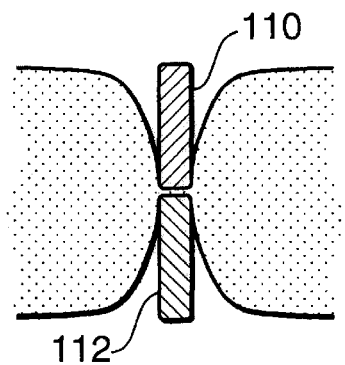
FIGS. 4A and 4B show cross-sections of jaws of the bipolar forceps that is cutting a tissue.
Figure 4B:
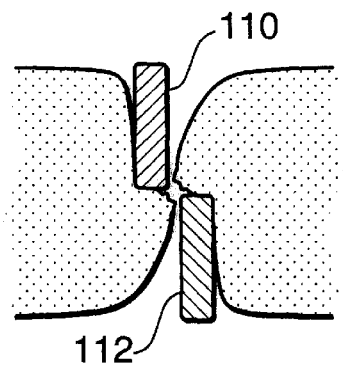

Next, a high frequency voltage is applied from the power supply between the jaws 110, 112 via the wires 122, 124 to cut and/or coagulate the target site as shown in FIG. 4A. Note that, the target site would be cut more smoothly if the jaws 110, 112 are rather shifted laterally to each other with respect to cutting direction as shown in FIG. 4B.

The bipolar forceps 100 as configured above is robust since the end effectors 106, 108, and also the shaft 132, 134 sustaining the end effectors 106, 108, are made of a metal such as stainless steel. Short circuit, however, does not occur between the end effectors during the application of high frequency voltage to the end effectors 106, 108, except when the jaws 110, 112 are closed and come into contact with each other, since each of the end effectors 106, 108 is supported by a separate shaft and thus insulated from each other. Further, although the shafts 132, 134 are also made of metal in the present embodiment, short circuit between the end effectors 106 and 108 does not occur even if fluid such as mucus adheres to and bridges the two shafts 132 and 134 since a cylindrical insulator is provided between the end effectors 106, 108 and the shafts 132, 134 to establish electric insulation of the end effectors 106, 108 against the shafts 132, 134.

Figure 5:
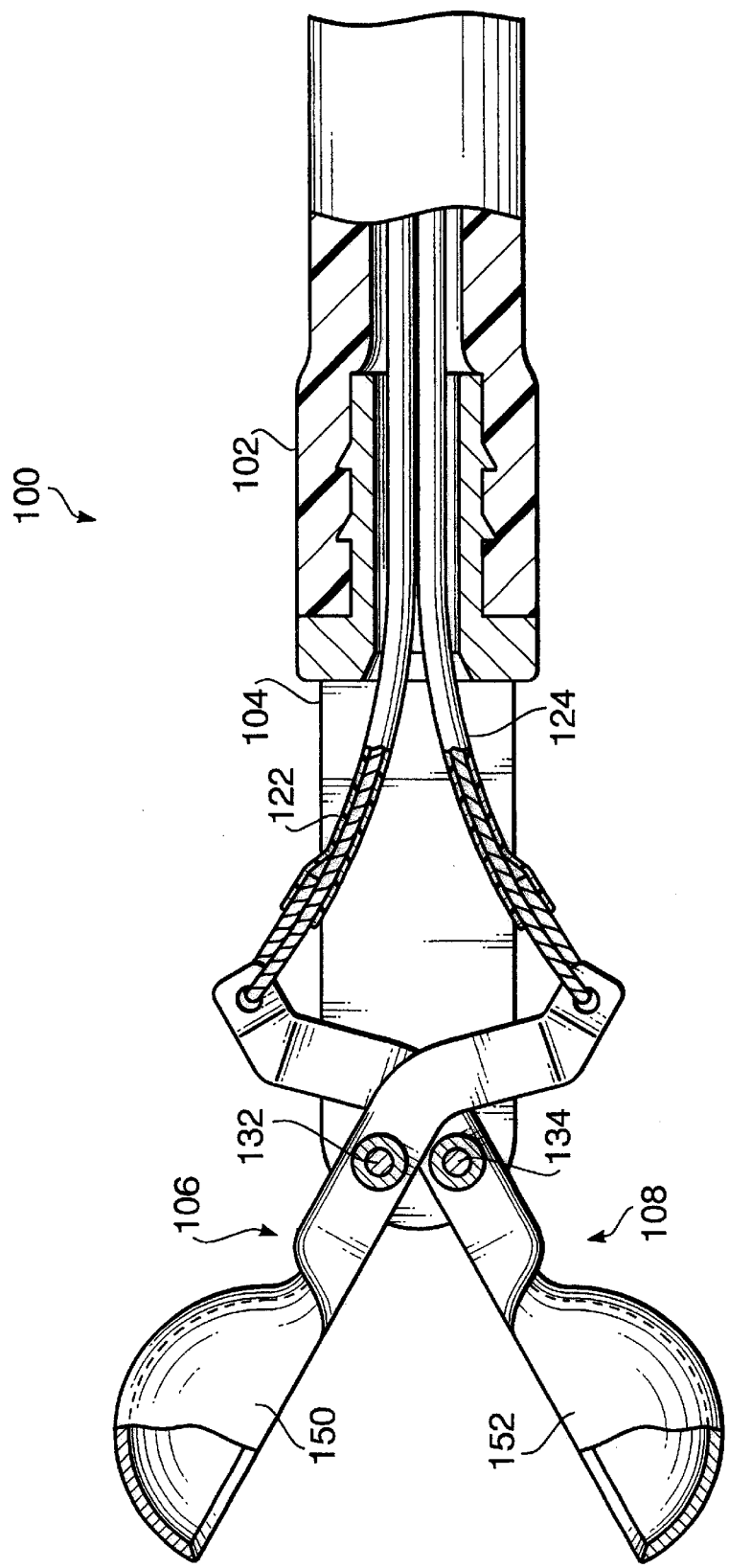
FIG. 5 is a partially cross-sectional side view of a distal end portion of a bipolar forceps for endoscopes according to another embodiment of the invention.
Figure 6:
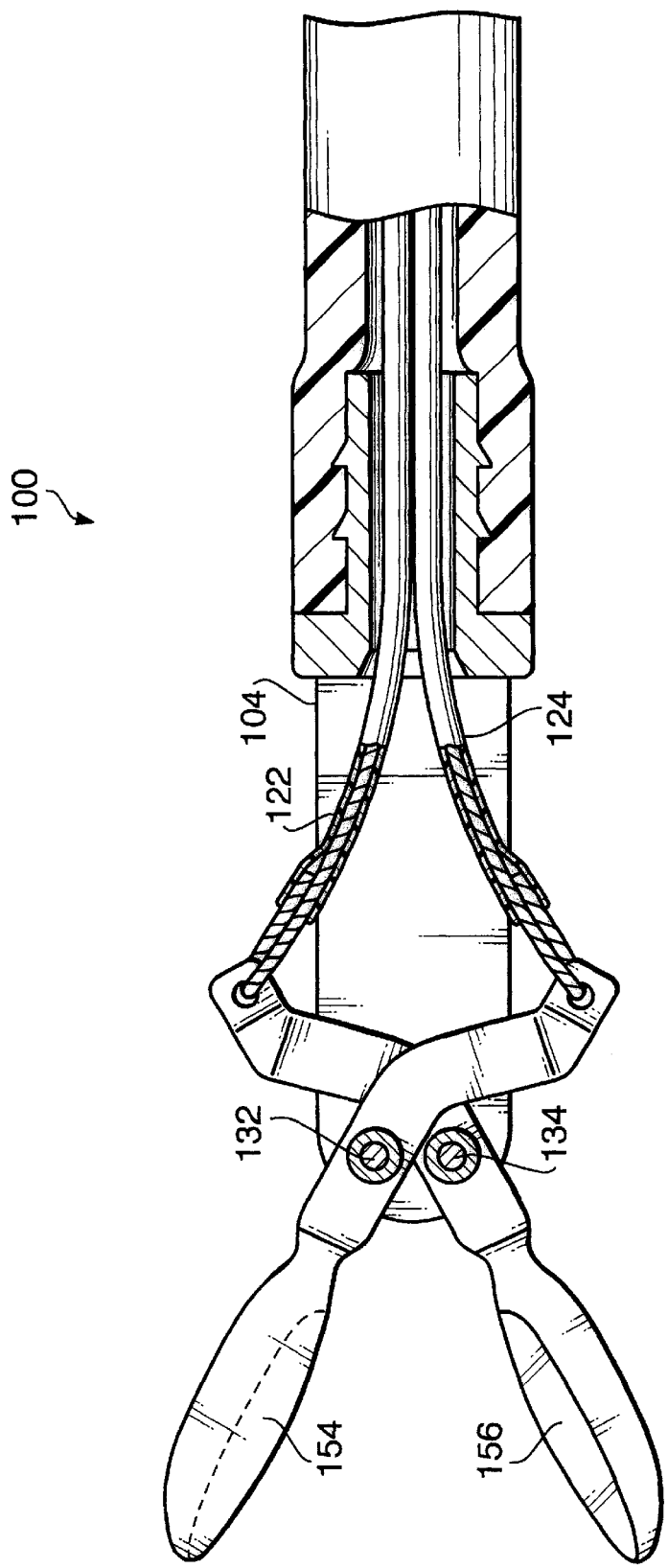
FIG. 6 is a partially cross-sectional side view of a distal end portion of a bipolar forceps for endoscopes according to still another embodiment of the invention.

Although the description above contains many specificities, these should not be construed as limiting the scope of the invention, but as merely providing illustrations of some of the presently preferred embodiments of this invention. For example, the jaws 132, 134 may be formed in various other shapes including cup type jaws 150, 152 as shown in FIG. 5 and trowel type jaws 154, 156 as shown in FIG. 6.

The present disclosure relates to the subject matter contained in Japanese Patent Application No. P2001-056752, filed on Mar. 1, 2001, which is expressly incorporated herein by reference in its entirety.

What is claimed is:

1. A bipolar forceps for endoscopes, comprising:
   a clevis having two arms, said two arms forming a slot therebetween;
   two shafts each sustained between said two arms spaced apart from each other;
   two end effectors each pivotably attached to a different one of said two shafts, respectively, such that said end effectors are able to move in a scissor-like action, said end effectors being made of conductive material to utilize said end effectors as electrodes for applying a high frequency voltage therebetween.

2. The bipolar forceps for endoscopes according to claim 1, wherein each of said shafts are arranged to cross said slot perpendicularly.

3. The bipolar forceps for endoscopes according to claim 1, wherein said two shafts are located on opposite sides with respect to the center axis of said clevis, respectively.

4. The bipolar forceps for endoscopes according to claim 3, wherein said two shafts are located at a same distance from the center axis of said clevis.

5. The bipolar forceps for endoscopes according to claim 1, wherein said two shafts are arranged in parallel to each other.

6. The bipolar forceps for endoscopes according to claim 1, wherein said shafts are made of metal.

7. The bipolar forceps for endoscopes according to claim 1, wherein said clevis is made of non-conductive material.

8. The bipolar forceps for endoscopes according to claim 1, wherein said end effectors are made of metal.

9. The bipolar forceps for endoscopes according to claim 1, further comprising two cylindrical insulators each provided on a different one of said two shafts, respectively, thereby electrically insulating said end effectors from said shafts.

10. The bipolar forceps for endoscopes according to claim 9, wherein said cylindrical insulator covers said shaft over the entire width of said slot.

11. The bipolar forceps for endoscopes according to claim 10, wherein said cylindrical insulator includes a small outer diameter portion for attaching said end effector thereon, said small outer diameter portion having an outer diameter smaller than the outer diameter of an adjacent portion of said cylindrical insulator for keeping said end effector in place.

12. The bipolar forceps for endoscopes according to claim 11, wherein one of said two cylindrical insulators has said small outer diameter portion at the end thereof located besides one of said two arms, and the other of said two cylindrical insulators has said small outer diameter portions at the end thereof located besides the other of said two arms.

13. The bipolar forceps for endoscopes according to claim 12, wherein each of said end effectors is bent between a distal end of said end effector and a portion being attached to said shaft such that at least said distal ends of said end effectors meet each other when said end effectors are closed.

* * * * *